United States Patent [19]

von Elbe et al.

[11] 4,027,042

[45] May 31, 1977

[54] COLOR EXTRACT FROM BEETS AND METHOD FOR THE PREPARATION OF SAME

[75] Inventors: Joachim von Elbe; Clyde H. Amundson, both of Madison, Wis.

[73] Assignee: Wisconsin Alumni Research Foundation, Madison, Wis.

[22] Filed: June 11, 1976

[21] Appl. No.: 695,104

Related U.S. Application Data

[63] Continuation of Ser. No. 514,647, Oct. 15, 1974, abandoned.

[52] U.S. Cl. .................................. 426/51; 426/52; 426/253; 426/540; 426/655; 195/74; 195/82; 195/96
[51] Int. Cl.$^2$ ......................................... A23L 1/277
[58] Field of Search ............... 426/49, 51, 52, 53, 426/60, 61, 62, 253, 540, 655; 195/8, 37, 39, 42, 57, 74, 82, 96

[56] References Cited

UNITED STATES PATENTS

| | | | |
|---|---|---|---|
| 2,543,083 | 2/1951 | White et al. | 195/2 |
| 2,863,805 | 12/1958 | Todd | 426/51 X |
| 3,737,324 | 6/1973 | Zinchenko et al. | 426/52 X |
| 3,783,099 | 1/1974 | Matonshek | 195/2 |

OTHER PUBLICATIONS

Takino et al, *Agr. Biol. Chem.*, vol. 28 No. 4, (1964), p. 255–256.

*Primary Examiner*—Raymond N. Jones
*Assistant Examiner*—Esther L. Massung
*Attorney, Agent, or Firm*—McDougall, Hersh & Scott

[57] ABSTRACT

The preparation of a coloring agent formed of beet pigment wherein the water soluble phase of the beets is subjected to fermentation for conversion of the soluble carbohydrates to an insoluble phase, leaving the beet pigment in a soluble phase, separating the soluble phase from the insoluble phase, and then removing aqueous medium from the soluble phase to produce a beet pigment concentrate.

24 Claims, No Drawings

COLOR EXTRACT FROM BEETS AND METHOD FOR THE PREPARATION OF SAME

This is a continuation of application Ser. No. 514,647, filed Oct. 15, 1974, now abandoned.

This invention relates to the recovery of pigment from beets and it relates more particularly to the process for the removal of components associated with the beet pigment to effect concentration or isolation of the beet pigment without destruction of the pigment and without undesirable effect on the beet pigment from the standpoint of physical characteristics and color.

The deep red color which characterizes beets is indicative of the presence of a vegetable dye or pigment. Interest exists in the utilization of such beet pigment as a vegetable color that could be used with safety in coloring other foods, pharmaceuticals and the like edible products or products which may be intentionally or unintentionally ingested in the human or animal system.

The difficulty arises in making such beet pigments available in an efficient and economical manner and in such concentration and yield as to enable practical use as a coloring agent for foods, pharmaceuticals and the like.

It is an object of this invention to provide a method for processing beets in a manner to effect removal of materials associated with the pigment in beets whereby the beet vegetable pigment can be made available as a coloring agent in sufficient concentration for use; in which such separation and concentration can be effected in a practical and economical manner without excessive loss of pigment or color, in which the nitrates and nitrites in the beet extracts are eliminated or reduced to negligible levels and in which such pigment recovery can be applied to whole beets or to portions of the beets that might otherwise be discarded as waste.

The process of this invention will be described with reference to the accompanying flow sheet which is given by way of illustration, but not by way of limitation, of the steps that are employed in the recovery of pigment from beets. For purposes of description, whole beets and beet waste will be treated as raw material, it being understood that the process is capable of being carried out with beets or beet waste, or mixtures thereof.

In brief, the beets are first reduced to a pulp. This can be accomplished in a number of ways with conventional equipment such as a grinder, homogenizer, high speed disintegrator and the like means. The result is a pulp of which about 10% by weight is solids, referred to generally as the fiber component, and the remainder of which is a liquid phase that contains the pigment along with other water solubles such as proteins, soluble pectins, and minerals or ash including nitrates and nitrites but in which the principal components are carbohydrates which are basically sucrose.

The liquid phase is separated from the solid phase by liquid-solid techniques, such as filtration, centrifugation, decantation and the like. When it is economically desirable to maximize the recovery of pigment, the separated solid phase can be washed one or more times with water, with the washings being joined with the separated liquid phase for the subsequent treatment by fermention. When use is made of a filtration system for liquid-solid separation, the desired washing can be carried out directly on the filter cake formed of the solids separated on the filter element. At this stage, the liquid phase will contain the beet pigment in a concentration which may range from 0.03 to about 0.2% by weight of the total liquid phase.

In order to effect the removal of the soluble carbohydrates for separation from the beet pigment, without injury to the pigment, the liquid phase is subjected to a fermentation wherein the soluble carbohydrates, nitrates, nitrites, and some of the protein fraction are utilized as food source by the yeast for cell production. These cells are separated by conventional liquid-solid techniques, such as filtration and the like.

Any type of glucose fermentation can be used, such as bacterial fermentation, but it is preferred to make use of aerobic fermentation in the presence of oxygen and a suitable inoculant. Various inoculants suitable for use in aerobic fermention can be employed, but best results are secured when use is made of a yeast, such as *Candida utilus*. With yeast of the type described, the oxygen is used up as fast as it is introduced thereby maintaining substantially zero oxygen levels in the liquor and thereby minimizng the effect of oxygen or oxidation of the beet pigment.

In the preferred practice, the yeast is introduced in an amount to maintain maximum yeast growth without increase in oxygen levels so as to effect conversion of the carbohydrates in the least possible time, or at maximum rate, without oxidizing the pigment. For this purpose, the yeast is introduced in an amount corresponding to at least 1/16 pound per pound of carbohydrate and preferably in the ratio of ¼ to 1 pound per pound of carbohydrate.

Pure oxygen can be used as the source of oxygen but such pure oxygen should not be employed at the start of the fermentation since it will tend to burn up the yeast. Substantially pure oxygen may be used when the oxygen content in the fermentation liquor is reduced to zero. It is preferred to make use of air as the source of oxygen throughout the fermentation process because of its low cost and ready availability.

Aerobic fermentation is carried out at room temperature or slightly above. Fermentation temperatures in excess of 40° C should not be employed, otherwise the yeast will be inhibited, and at temperatures below ambient, fermentation falls to a negligible rate. The pH of the liquor should be maintained slightly on the acid side during fermentation, such as within the range of pH 4 to 6, and preferably at a pH of about 5.

The rates of oxygen introduction will depend somewhat upon the yeast employed, the reaction rate, the amount of carbohydrate and the fermentation temperature. The rate of oxygen introduced is readily determined during operation to maintain maximum yeast growth but at a level not to exceed the rate of consumption of oxygen thereby to maintain substantially zero oxygen level during fermentation.

In the event that the beets do not contain sufficient soluble nitrates or phosphates, nutrients can be added to the fermentation liquor in the form of ammonia and/or soluble phosphate salt.

During fermentation the soluble carbohydrates and some of the crude protein are converted to single cell proteins which can be separated from the remaining liquor by conventional liquid-solid separation techniques, such as filtration, centrifugation and the like. The yeast cells thus separated can be used in human foods or animal feed. This by-product is of considerable value thereby enhancing the economics in the recovery of the beet pigment as a coloring material.

By way of modification, instead of subjecting the original beet pulp to liquid-solid separation and washing to effect removal of fiber, the entire pulp can be subjected directly to the fermentation step, with the fiber retained in the liquor. Under such conditions, fermentation still operates to convert the carbohydrates and the crude proteins to single cell proteins, without modification of the original fiber. As a result, subsequent liquid-solid separation of the fermentation reaction product will yield a protein-enriched cellulose fiber which finds valuable use as animal feed.

The liquor remaining after extraction of the solids from the fermentation product contains the beet pigment in a concentration (calculated on a dry weight basis) or 1–10% by weight.

The liquor can be used as a coloring material but it is preferred to effect concentration of the liquor by removal of water to increase the content of beet pigment to within the range of 0.5 to 5% by weight, when the liquor is to be used as a vegetable coloring agent.

The liquor can be reduced to dry powder form by conventional technique, such as spray drying, preferably under subatmospheric conditions, or freeze drying. Before utilization of any one or more of the described drying techniques, it is desirable, though not essential, to concentrate the liquor, as by evaporation or distillation, to remove a major portion of the aqueous medium. The dried powder will contain the beet pigment in an amount corresponding to the amount contained in the liquor when calculated on the dry weight basis, such as an amount within the range of 1–10% by weight, depending greatly upon the variety of beet used as the raw material.

A dry particulate or powdered concentrate containing the beet pigment in much higher concentrations, such as in amounts up to 40–70% by weight, can be achieved by processing the liquor and preferably a concentrated liquor by such techniques as reverse osmosis, molecular sieving, and/or by chromatographic separation. Concentration of 50% by weight beet pigment in a dry powder form has been produced by the use of a Sephadex G-25 column.

The concentration of beet pigment in the liquid or powder form, prepared in accordance with the practice of this invention, can vary quite widely depending greatly upon the variety of beet that is used and the extent to which the fermentation reaction is carried out for extraction of components originally associated with the pigment in the raw beet. However, because of the intense color made available from the vegetable pigment, it has been found sufficient for practical use to reduce the beet to form a liquor containing 0.1 to 1.0% by weight pigment or to a particulate or powdered material containing at least 1 and preferably 3–70% by weight beet pigment.

The following example is given by way of illustration but not by way of limitation of the practice of this invention in the separation of beet pigment for use as a coloring agent.

EXAMPLE

The beet roots were washed and dried. Ascorbic acid was added to prevent browning oxidation. The mixture was pulped in a Fitzpatrick Mill Model D equipped with a ¼ inch mesh screen and pressed. The juice thus extracted was centrifuged at 1000 × g for 15 min. to remove insolubles. Prior to fermentation the juice was subjected to ultrafiltration (cellulose acetate hollow fiber, 30,000 nominal weight cut-off) at room temperature under 8 psi nitrogen for the removal of macromolecules i.e. pectins.

The juice was subjected to fermentation to remove carbohydrates, mainly sucrose, and most of the crude soluble protein. The inoculum was *Candida utilus* (¼ lb. yeast per 1 lb. of carbohydrate). During fermentation the temperature was maintained at 30 ± 2 C; the air flow at 1750 cc/min and the pH was controlled with 7% NaOH or 5% HCl at pH 5.0 ± 0.3. These conditions afforded optimum growth for yeast and maximum utilization of carbohydrates. Time of the fermentation was 110 min/1% sucrose of juice.

Specific analyses of the juice before and after fermentation were:

TABLE 1

| SAMPLE DATA FOR FERMENTED JUICE | | |
|---|---|---|
| Initial Juice Analysis | $10^2$g/g Sample | Percent of Total Solids |
| Total Solids (TS) | 7.878 ± 0.022 | |
| Ash | 0.611 ± 0.008 | 7.8 ± 0.1 |
| Crude Protein | 0.756 ± 0.008 | 9.6 ± 0.1 |
| Sucrose$^a$ | 6.075 ± 0.158 | 77 ± 2 |
| Glucose | Not Detn. | Not Detn. |
| Botacyanine | 0.074 ± 0.005 | 0.94 ± 0.06 |
| Unaccountable Fraction | 0.362 ± 0.201 | 5 ± 3 |
| After Ultrafiltration | | |
| Total Solids | 7.012 ± 0.035 | |
| Ash | 0.554 ± 0.021 | 7.9 ± 0.3 |
| Crude Protein | 0.731 ± 0.014 | 10.4 ± 0.2 |
| Sucrose | 5.529 ± 0.280 | 79 ± 4 |
| Glucose | 0.092 ± 0.005 | 1.7 ± 0.1 |
| Botacyanine | 0.080 ± 0.007 | 1.1 ± 0.1 |
| Unaccountable Fraction | 0.026 ± 0.362 | 0 |
| After Fermentation | | |
| Total Solids | 1.200 ± 0.012 | |
| Ash | 0.631 ± 0.024 | 53 ± 2 |
| Crude Protein | 0.138 ± 0.001 | 12 ± 0 |
| Sucrose | b | b |
| Glucose | 0.049 ± 0.001 | 4.1 ± 0.1 |
| Botacyanine | 0.081 ± 0.007 | 6.8 ± 0.6 |
| Unaccountable Fraction | 0.301 ± 0.045 | 25 ± 4 |

$^a$Glucose included.
$^b$Below limits of method.

The fermented juice was centrifuged to remove yeast cells and concentrated 10:1 under vacuum. To remove the salts which were the majority of the solids, the juice was acidified to pH 2.0 with HCl and chromatographed on a column (75 × 5 cm) packed with Sephadex G-25 fine. The flow rate was 5.95 ml distilled water/min. The final pigment fraction was dried and had a betacyanine content of 55% and was free of nitrates and nitrites.

We claim:
1. The process of treating beets to recover beet pigment in a concentration and form suitable for use as a vegetable coloring agent, comprising the steps of reducing the beets to an insoluble phase and an aqueous phase in which the beet pigment along with other soluble carbohydrates, nitrates, nitrites and proteins are present in the dissolved state, subjecting the water soluble portions of the beets to carbohydrate fermentation with or without prior separation of the insoluble phase, whereby soluble carbohydrates, and some crude proteins are converted to insoluble fermentation reaction products while the beet pigment remains in the dissolved state in the aqueous phase, and separating the soluble phase containing the beet pigment from the insoluble phase.

2. The process as claimed in claim 1 in which the soluble phase is separated from the insoluble phase by filtration.

3. The process as claimed in claim 1 in which the soluble phase is separated from the insoluble phase by decantation.

4. The process as claimed in claim 1 in which the soluble phase is separated from the insoluble phase by centrifugal separation.

5. The process as claimed in claim 1 in which the fermentation comprises a bacterial fermentation.

6. The process as claimed in claim 1 in which the fermentation is an aerobic fermentation carried out while the pH is slightly on the acid side and at a temperature of from ambient to 40° C, in which a yeast inoculant and an oxygen containing gas are introduced into the aqueous phase.

7. The process as claimed in claim 6 in which the oxygen containing gas is air introduced into the liquid phase.

8. The process as claimed in claim 6 in which the yeast is introduced in an amount to maintain a maximum yeast growth without increase in oxygen level.

9. The process as claimed in claim 6 in which the yeast is introduced in an amount within the range of 1/16 to 1 pound per pound of carbohydrate in the soluble phase.

10. The process as claimed in claim 6 in which the fermentation is carried out while maintaining the pH within the range of 4 to 6.

11. The process as claimed in claim 6 in which the oxygen is introduced at a rate to maintain maximum yeast growth but not to exceed the rate of consumption of oxygen.

12. The process as claimed in claim 6 which includes the addition of nutrient selected from the group consisting of ammonia or ammonium salts and soluble phosphoric acid salts.

13. The process as claimed in claim 1 in which the separated water-soluble phase contains the beet pigment in a concentration within the range of 1–10% by dry weight.

14. The process as claimed in claim 1 in which the separated water-soluble phase is concentrated by the removal of water to increase the concentration of the beet pigment to about 2% by weight.

15. The process as claimed in claim 1 in which the separated water-soluble phase is reduced to dry powder form in which the beet pigment is present in a concentration of 1–70% by weight.

16. The process as claimed in claim 15 in which the water-soluble phase is reduced to dry powder form after reverse osmosis.

17. The process as claimed in claim 15 in which the water-soluble phase is reduced to dry powder form after molecular sieving.

18. The process as claimed in claim 15 in which the water-soluble phase is reduced to dry powder form after chromatographic separation.

19. A vegetable color composition prepared by the process of claim 1 containing beet pigment in solution in aqueous medium in a concentration of 1–10% by dry weight.

20. A vegetable color composition prepared by the process of claim 15 containing beet pigment in dry powder form in a concentration within the range of 1–70% by weight.

21. The process as claimed in claim 1 in which the insoluble phase is separated from the aqueous phase prior to fermentation of the aqueous phase.

22. The process as claimed in claim 1 in which the insoluble phase, which contains the beet fiber, is separated from the aqueous phase after fermentation whereby the insoluble phase separated from the aqueous phase includes the beet fiber and the insoluble fermentation reaction product.

23. The protein enriched beet fiber produced by the method of claim 22.

24. The process of treating beets to recover beet pigment in a concentration and form suitable for use as a coloring agent, comprising the steps of reducing the beets to an insoluble phase and a liquid phase in which the beet pigment along with other water soluble carbohydrates, nitrates, nitrites and protein are present in the dissolved state in the liquid phase, subjecting the liquid phase to aerobic fermentation, with or without prior separation of the insoluble phase, with the introduction of an inoculant in the form of yeast and an oxygen containing gas, while the liquid phase is at a pH within the range of 4 to 6 and at a temperature within the range of about ambient to 40° C to convert soluble carbohydrates, nitrates, nitrites and protein to insoluble fermentation products, and separating the resulting liquid phase into a solid component and a liquid component, the latter of which still contains beet pigment in the solubilized state.

* * * * *

UNITED STATES PATENT OFFICE
CERTIFICATE OF CORRECTION

Patent No. 4,027,042          Dated    May 31, 1977

Inventor(s)  Joachim von Elbe and Clyde H. Amundson

It is certified that error appears in the above-identified patent and that said Letters Patent are hereby corrected as shown below:

column 3, line 19, change "0.5 to 5%" to -- 0.5 to 2% --

Signed and Sealed this

Twentieth Day of September 1977

[SEAL]

Attest:

RUTH C. MASON
Attesting Officer

LUTRELLE F. PARKER
Acting Commissioner of Patents and Trademarks